United States Patent
Rosson et al.

(10) Patent No.: US 9,441,200 B2
(45) Date of Patent: Sep. 13, 2016

(54) COMPOSITIONS AND METHODS FOR IMPLANTATION OF ADIPOSE TISSUE AND ADIPOSE TISSUE PRODUCTS

(75) Inventors: Gedge Rosson, Baltimore, MD (US); Jennifer H. Elisseeff, Los Angeles, CA (US); Zayna Nahas, Palo Alto, CA (US); Zhaoyang Ye, Baltimore, MD (US); Alexander Hillel, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 870 days.

(21) Appl. No.: 12/867,045

(22) PCT Filed: Feb. 11, 2009

(86) PCT No.: PCT/US2009/000887
§ 371 (c)(1),
(2), (4) Date: Mar. 28, 2011

(87) PCT Pub. No.: WO2009/102452
PCT Pub. Date: Aug. 20, 2009

(65) Prior Publication Data
US 2011/0183001 A1   Jul. 28, 2011

Related U.S. Application Data

(60) Provisional application No. 61/065,322, filed on Feb. 11, 2008.

(51) Int. Cl.
| A61K 35/12 | (2015.01) |
| A61K 35/32 | (2015.01) |
| A61K 35/36 | (2015.01) |
| C12N 5/00 | (2006.01) |
| C12N 5/077 | (2010.01) |
| A61K 35/35 | (2015.01) |

(52) U.S. Cl.
CPC ............. *C12N 5/0653* (2013.01); *A61K 35/35* (2013.01); *A61K 35/12* (2013.01); *C12N 2533/30* (2013.01); *C12N 2533/80* (2013.01)

(58) Field of Classification Search
None
See application file for complete search history.

(56) References Cited

U.S. PATENT DOCUMENTS

| 2002/0076400 A1 * | 6/2002 | Katz et al. ................. 424/93.21 |
| 2005/0033449 A1 | 2/2005 | Ashman |
| 2005/0147642 A1 | 7/2005 | Laredo et al. |
| 2006/0159664 A1 * | 7/2006 | Pandit et al. ................ 424/93.7 |

FOREIGN PATENT DOCUMENTS

| WO | 00/53795 A1 | 9/2000 |
| WO | 2006/062989 A1 | 6/2006 |
| WO | 2007-037572 A1 | 4/2007 |
| WO | WO 2007037572 A1 * | 4/2007 |

OTHER PUBLICATIONS

Gilbert et al., Biomaterials, vol. 27, pp. 3675-3683 (2006).*
Kimura, Y., el al., "Adipose tissue engineering based on human preadipocytes combined with gelatin microspheres containing basic fibroblast growth factor", Biomaterials, 2003, vol. 24, pp. 2513-2521.
Heimburg, D.V., et al., "Human preadipocytes seeded on freeze-dried collagen scaffolds investigated in vitro", Biomaterials, 2001, vol. 22, pp. 429-438.

* cited by examiner

*Primary Examiner* — Soren Harward
*Assistant Examiner* — Paul D. Pyla
(74) *Attorney, Agent, or Firm* — John Hopkins Technology Transfer (57) ABSTRACT

The invention provides compositions and methods for the preparation of biocompatible biomaterials from adipose tissue. Biocompatible biomaterials are cellular or acellular biomaterials. The invention further provides methods of use of the biocompatible biomaterials.

6 Claims, 6 Drawing Sheets

COMPOSITIONS AND METHODS FOR IMPLANTATION OF ADIPOSE TISSUE AND ADIPOSE TISSUE PRODUCTS

RELATED APPLICATIONS

The instant application is a 35 U.S.C. §371 U.S. national entry of International Application PCT/US2009/000887 (WO 2009/102452) having an Internationally filing date of Feb. 11, 2009 which claims the benefit of U.S. Provisional Patent Application Ser. No. 61/065,322 filed on Feb. 11, 2008 both of which are incorporated herein by reference in their entirety.

BACKGROUND

The field of regenerative medicine aims to provide tissue substitutes for reconstruction secondary to trauma, disease or congenital abnormalities. While biomaterials and cells are often employed to regenerate new tissues, these methods tend to be costly and require significant time for new tissue formation. Restoration of soft tissue form is critical for a number of applications including trauma reconstruction, breast reconstruction, and cosmetics (nasolabial folds, wrinkles, etc). In general there are two approaches today; 1.) injection/transfer of biological tissue (fat) or 2.) injection or implantation of a synthetic or naturally derived material. In both cases, the transplanted tissue or biomaterial will eventually be degraded and replacement is required.

Reconstruction using patient tissue can provide permanent restoration of tissue in some situations. However, such procedures also have their limitations. Breast reconstruction after mastectomy can include the use of tissue flaps of muscle and adipose tissue either from the abdomen or back which are pulled over to the reconstruction site. Such flaps are necessarily limited in size by the amount of tissue present in the woman for use, and transfer of muscle from the abdomen or back can extend recovery time and result in donor site morbidity. The persistence of fat transfer varies widely with reports of anywhere between 30-90%. Persistence is also often surgeon and technique dependent. Such loss of persistence requires multiple procedures to maintain the desired correction. The donor site morbidity associated with autologous fat transfer is also a significant concern. In addition, implanted adipose tissue often leads to post-operative calcifications. This phenomena is of particular importance for women with a history of breast cancer undergoing breast reconstruction following mastectomy, as the calcifications may interfere with mammography readings and result in multiple, unnecessary breast biopsies and anxiety. Finally, for many patients undergoing chemotherapy and radiation for cancer, the associated cachexia leaves them without the adipose volume they would require for autologous fat transfer.

SUMMARY OF THE INVENTION

The invention provides methods for preparation of processed adipose tissue (PAT) including sequentially obtaining mammalian tissue comprising solid adipose, such as subcutaneous adipose tissue, isolating the adipose from the non-adipose material in the tissue; for example by scraping, and manipulating the adipose with one or more buffers sequentially to promote lipid and cell removal to prepare processed adipose tissue. The mammalian adipose tissue can be obtained from any mammal, most conveniently from larger mammals to provide sufficient starting material. The method optionally includes sterilizing the processed adipose tissue, for example by irradiation or contact with an appropriate gas.

Buffers for use during the manipulation of the isolated adipose include buffers of physiological pH and ionic strength, such as phosphate buffered saline (PBS) or physiological saline. Buffers can further compounds such as weak acid, a weak organic acid, a non-ionic detergent, or a bile acid, or a combination thereof, to promote decellularization or lipid extration of the solid adipose.

The invention provides methods for forming the processed adipose tissue of the invention into particles, for example to facilitate administration. The invention provides methods for optionally combining the processed adipose tissue with a biopolymer scaffold. The biopolymer scaffold can be previously cross-linked (e.g., cross-linked hyaluronic acid), or include functional groups to allow the biopolymer to form a cross-linked structure in the absence of any further agents (e.g., functionalized chondroitin sulfate). Alternatively, the biopolymer scaffold can require the use of cross-linking agents and polymerization initiators. Polymerization initiators can include chemical initiators or light. The invention provides methods for polymerization of the biopolymer scaffold.

The invention further provides methods for preparation of a cellular adipose biocompatible biomaterial including obtaining an adipose cell; and contacting the adipose cell with a biocompatible biopolymer and a surfactant. The adipose cell can be obtained from a liquid adipose, e.g., a lipoaspirate, or solid adipose that has been processed to provide isolated adipose cells to be combined with the biopolymer and the surfactant. The biocompatible polymer can be cross-linked prior to contacting the polymer with the cell (e.g., cross-linked hyaluronic acid), be functionalized to include reactive groups to allow for the formation of cross-links (e.g., functionalized chondroitin sulfate), or require the addition of additional agents to promote cross-linking (e.g. PEG-DA). The invention further provides methods for including cross-linking the biopolymer using a cross-linking agent and optionally a polymerization agent. Polymerization is optionally activated by a polymerization initiator such as eosin Y, 1-vinyl 2-pyrrolidone NVP, and triethanolamine; and Igacure D2959, optionally further including light. The invention provides methods wherein the surfactant is a non-ionic detergent such as a straight chain polyether surfactants having an HLB value greater than or equal to 18.

The invention further provides compositions made by any of the methods of the invention, including any processing intermediates.

The invention further provides for the use of any of the compositions of the instant invention as biomaterials, including any processing intermediates, for example for tissue reconstruction or restoration. The invention provides the compositions of the instant invention in an appropriate carrier for administration (e.g., saline.)

The invention further provides kits for making any of the compositions of the invention. The invention further provides kits for using any of the compounds of the invention. The kits of the invention can further include instructions for use.

DEFINITIONS

As used herein, "acellular" is understood as a material that contains no cells, viable or non-viable, whole or fragments, or sufficiently few cells or cellular material such that the cells present are not sufficient to generate an immune response in the subject into which the material is implanted. Cells may be removed from source tissue, for example, by mechanical or chemical methods, or a combination thereof.

An "acellular adipose biocompatible biomaterial", also referred to as "processed adipose tissue" or "PAT" is understood as a composition derived from adipose tissue obtained from a donor, for example from a live donor (e.g., autologous donation, byproduct of cosmetic surgical procedure such as liposuction or abdominoplasty) or tissue bank (e.g., live donor, cadaver donor). The composition can be derived from subcutaneous fat, visceral fat, white fat, brown fat, a mixed cell population including fat tissue (e.g., a lipoaspirate) or any combination thereof. In a first step, the adipose separated from the non-adipose material in the tissue sample, e.g., by scraping the adipose from the dermis or surrounding organ, partitioning the lipoaspirate, etc. to prepare isolated adipose. The isolated is treated with chemical and/or mechanical methods to remove the fat cells and the lipid components. The material is preferably treated to kill any remaining cells not removed by the process prior to implantation in a subject. As the material is acellular, it is non-immunogenic. Therefore, the composition can be implanted non-autologously. The composition can be combined with other materials prior to implantation into the subject, including cells or cellular material.

The terms "active agent," and "biologically active agent" are used interchangeably herein to refer to a chemical or biological compound that induces a desired pharmacological, physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, it is to be understood that applicants intend to include the active agent per se as well as pharmaceutically acceptable, pharmacologically active salts, esters, amides, prodrugs, metabolites, analogs, etc.

As used herein, "autologous" transplantation, donation, and the like is understood as a procedure in which the source of adipose tissue for implantation into the subject is derived from the same subject. Autologous transplantation or donation can include processing of the tissue between harvesting of the tissue from the subject and re-implantation of the tissue into the subject.

The term "bile acid" is understood as a steroid acids found predominantly in the bile of mammals. Bile acids can act as detergents and surfactants. Bile acids include, but are not limited to taurocholic acid, glycocholic acid, cholic acid, chenodeoxycholic acid, deoxycholic acid, and lithocholic acid.

The term "biocompatible" when used in relation to polymers are art-recognized. For example, biocompatible polymers include polymers that are neither themselves toxic to the host at the concentrations and quantities used (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75%, 70%, 60%, 50% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 μL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, polymers, polymer matrices, and formulations of the present invention may also be evaluated by well-known in vivo tests, such as subcutaneous implantations in rats to confirm that they do not cause significant levels of irritation or inflammation at the subcutaneous implantation site.

Biocompatible materials can also include naturally derived products appropriate for implantation into a subject, such as the acellular adipose biomaterial provided herein.

As used herein, "biocompatible biomaterial" are materials that can be used for tissue reconstruction or cosmetic procedures such as smoothing of wrinkles that are acceptable for use in a mammal, preferably in a human subject.

"Contacting" as used herein is understood as bringing two or more components into sufficient proximity (e.g. a biocompatible polymer, a cross-linking agent, a surfactant, and an adipose cell; subcutaneous adipose tissue and peracetic acid) for sufficient time and under appropriate condition of temperature, pressure, pH, ionic strength, etc. to allow for the interaction of the two or more components, e.g., formation of a gelled biopolymer matrix including adipose cells; decellularization of adipose tissue. Contacting in the context of the invention can occur in a reaction vessel such as a tube, or in a subject in a body cavity to be filled with a composition of the invention.

"Cross-linked" as used herein refers to a composition containing intermolecular cross-links and optionally intramolecular cross-links arising from the formation of covalent bonds, ionic bonds, hydrogen bonding, or any combination thereof. "Cross-linkable" refers to a component or compound that is capable of undergoing reaction to form a cross-linked composition.

The polymerizable agent of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The polymerizable agent should be substantially hydrophilic and biocompatible.

As used herein, "detecting", "detection" and the like are understood that an assay or method performed for identification of a specific analyte in a sample. The amount of analyte detected in the sample can be none or below the level of detection of the assay or method.

The term "gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two dimensional surface.) "Gelation time," also referred to herein as "gel time," refers to the time it takes for a composition to become non-flowable under modest stress. This is generally exhibited as reaching a physical state in which the elastic modulus G' equals or exceeds the viscous modulus G", i.e., when tan (delta) becomes 1 (as may be determined using conventional rheological techniques).

"Hyaluronic acid" (HA) (also known as "hyaluronan" or "hyaluronate") is a non-sulfated glycosaminoglycan distributed widely throughout connective, epithelial, and neural tissues. It is one of the chief components of the extracellular matrix, contributes significantly to cell proliferation and migration, and may also be involved in the progression of some malignant tumors. The repeating disaccharide unit of HA is $(-4GlcUA\beta 1-3GlcNAc\beta 1-)_n$. Hyaluronic acid can be 25,000 disaccharide repeats in length. Polymers of HA can range in size from 5 to 20,000 kDa in vivo. Hyaluronic acid for use in the invention can have a molecular weight of about 5, 10, 25, 50, 100, 500, 1000, 2000, 5000, 7500, 10,000, 15,000, or 20,000 kDa, or any range between any of the two molecular weights provided. The specific size of the HA to be used is a matter of choice of the end user. For example, it is well understood that higher molecular weight HA has better viscosity for many applications. Lower molecular weight HA is angiogenic, however, lower molecular weight HA also produces a stronger inflammatory reaction than higher molecular weight HA. Such considerations are well understood by those of skill in the art.

As used herein, a "hydrogel" is understood as a hydrophilic cross-linked polymer capable of containing a large volume fraction of water. More preferably hydrogels according to the present invention can contain greater than about 70-90 volume % water. When a hydrophilic polymer is formed in situ, it may inherently acquire water from its environment or from solutions used to create the hydrogel.

As used herein, "isolated" particularly as used in "isolated adipose" is understood as separating the non-adipose tissue or cells from the adipose extracellular matrix, tissue, or cells to allow for preparation of one or more of the biomaterials of the instant invention. "Isolated adipose" can include solid isolated adipose, e.g., from tissue samples e.g., such as subcutaneous fat, or liquid isolated adipose, e.g., from lipoaspirate. Isolation does not require that the material is completely free of non-adipose material. Isolated adipose is understood as containing at least 70%, 80%, 85%, 90%, 95%, or 98% adipose cells, tissue, extracellular matrix, etc. For example, adipose can be isolated from a tissue sample including subcutaneous fat by scraping. Adipose can be isolated from lipoaspirate by density using methods known in the art.

As used herein, "kits" are understood to contain two or more components for use with a method of the invention, in appropriate packaging or with instructions for use.

As used herein, "lipoaspirate" is an otherwise disposable byproduct of cosmetic surgery procedures such as liposuction.

As used herein, "mammal" is understood as any animal of the class mammalian. Mammal is understood to include, but is not limited to human and non-human primates, pigs, dogs, cats, cows, mice, rats, horses, and rabbits.

As used herein, "manipulating" is understood as manually (e.g., like kneading bread) or mechanically (e.g., using a mixer, homogenizer, or blender) to work, press, or divide a mass of non-liquid material, e.g., adipose, to contact the material throughout with the buffer. Manipulating can be performed, for example, to promote decellularization and/or lipid removal from adipose.

"Non-ionic detergent" as used herein is understood to include, for example, ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Triton® X-100, Triton® X-114, Pluronics from BASF (such as those listed as surfactants below) Tween® 20, Tween® 80, from ICI Americas Inc., Wilmington, Del., which is a polyoxyethylated (20) sorbitan monolaurate, Iconol™ NP-40, from BASF Wyandotte Corp. Parsippany, N.J., which is an ethoxylated alkyl phenol (nonyl); octyl-glucoside, and octyl-thioglucoside.

"Obtaining" is understood herein as manufacturing, purchasing, or otherwise coming into possession of.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers for use in the invention may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

As used herein, "plurality" is understood to mean more than one. For example, a plurality refers to at least two, three, four, five, 10, 25, 50, 100 or more.

"Polyethylene glycol" (PEG) (also known as poly(ethylene oxide) (PEO) or polyoxyethylene (POE)) has the formula HO—(CH$_2$—CH$_2$—O—)$_n$—H and are typically linear (i.e., unbranched) molecules. Polyethylene glycol for use in the compositions and methods of the instant invention have a molecular weight of about 1000 MW to 10,000 MW.

A polymerizable mixture as used herein is any suitable polymerizable polymer, monomer, or mixture of monomers and polymers that forms: a covalently crosslinked network, with or without the presence of a polymerization initiator, an ionically crosslinked network, or blends of covalently and ionically crosslinked networks. Polymerizable mixtures in accordance with the present invention must be able to form polymerized networks that are non-toxic to the cells being encapsulated.

A photopolymerizable polymer is any suitable polymer that forms a covalently crosslinked network using radiation provided by an external source, or blends of covalently and ionically crosslinkable or hydrophilic polymers which, when exposed to radiation from an external source, form semi-interpenetrating networks having cells suspended therein. Photopolymerizable mixtures in accordance with the present invention must be able to form polymerized networks that are non-toxic to the cells being encapsulated.

A polymerization initiator is any substance that initiates crosslinking of the polymer to form a hydrogel network, and includes redox agents, divalent cations such as calcium, and substances that form active species when exposed to visible light and/or UV radiation. A photoinitiator is a specific type of polymerization initiator that generates an active species when exposed to UV light and/or visible light, and can be used to initiate polymerization (i.e., crosslinking) of the photopolymerizable mixtures. Polymerization initiators and photoinitiators in accordance with the present invention must be non-toxic to the cells being encapsulated when used in the amounts required to initiate crosslinking of the polymerizable mixtures.

A hydrogel for encapsulating living cells is a hydrophilic polymer network with a high water content. Such hydrogels in accordance with the present invention, may have, for example, a water content greater than about 70-90%. Such hydrogels in accordance with the present invention are non-toxic to the encapsulated cells and permit the movement of nutrients to the cells, and waste products away from the cells, through the polymer network.

A "polymerizing initiator" refers to any substance or stimulus, that can initiate polymerization of monomers or macromers by free radical generation. Exemplary polymerizing initiators include electromagnetic radiation, heat, and chemical compounds.

The process of "promoting decellularization and lipid extraction" is understood as chemical treatment and/or manipulation of a sample, such as a tissue sample, to remove cells and lipids from the material. The process can include serial rounds of washing and manipulation of the sample in the presence of one or more buffers.

As used herein, a "solution" means a solution, a suspension, or a colloid.

The term "space," is used herein to described the location of where a composition of the instant invention is injected or implanted to solidify, and is defined broadly and may include a cavity formed in a mold, a cavity surgically formed in tissue, or a naturally existing cavity in tissue that can be surgically accessed, a wrinkle or other tissue aberration to be repaired using the compositions and methods of the invention.

As used herein, "subject" is understood as an animal, preferably a mammal such as a mouse, rat, dog, cat, monkey, cow, pig, or a human. A human subject can also be known as a patient.

"Surfactant" as used herein is a composition for helping emulsification of fat tissue in the described biomaterial, hydrogel, or other biomaterial solution comprising a straight chain polyether surfactant having an HLB (hydrophilic-lipophilic balance) value greater than or equal to 18 or any of combination, which is proved to be safe for clinical use.

Straight chain polyether surfactants are available from commercial sources including, but not limited to, BASF Wyandotte Corp (Wyandotte, Mich) as "Pluronic™". The HLB of a surfactant is known to be a major factor in determining the emulsification characteristics of a polyether surfactant. In general, surfactants with lower HLB values are more lipophilic, while surfactants with higher HLB values are more hydrophilic. The HLB values of various poloxamines and poloxamers are provided by BASF Wyandotte Corp.

Suitable straight chain polyether surfactants having an HLB value greater than or equal to 18, include for example but are not limited to Pluronic $F_{38}$™ (BASF) having a HLB of 31 and average molecular weight (AMW) of 4700; Pluronic $F_{68}$™ (BASF) having a HLB of 29 and AMW of 8400; Pluronic 68LF™ (BASF) having a HLB of 26 and AMW or 7700; Pluronic $F_{77}$™ (BASF) having a HLB of 25 and AMW of 6600; Pluronic $F_{87}$™ (BASF) having a HLB of 24 and AMW of 7700; Pluronic $F_{88}$T$^M$ (BASF) having a HLB of 28 and AMW or 11400; Pluronic $F_{98}$™ (BASF) having a HLB of 28 and AMW of 13000; Pluronic $F_{108}$™ (BASF) having a HLB of 27 and AMW of 14600; Pluronic $F_{127}$™ (BASF) having a HLB of 22 and AMW of 12600; Pluronic $L_3^{5}$™ (BASF) having a HLB of 19 and AMW of 1900; Tetronic 707™ (BASF) having a HLB of 27 and AMW of 12200; Tetronic 908™ (BASF) having a HLB of 31 and AMW of 25000. The preferred straight chain poly(ethylene oxide-propylene oxide-ethylene oxide) (PEO-PPO-PEO) block copolymers having HLB value greater than or equal to 18, Pluronic surfactants, are Pluronic $F^{38}$™, Pluronic $F_{68}$™, Pluronic 68LF™ Pluronic $F_{77}$™, Pluronic $F_{87}$™, Pluronic $F_{88}$™, Pluronic $F_{98}$™, Pluronic $F_{108}$™, and Pluronic $F_{127}$™. More preferred Pluronic surfactants are Pluronic $F_{127}$™

To obtain the required HLB of fat tissue, polyether surfactants or polyether surfactants in combination in the aqueous composition is from about 2.0 to 10.0 weight percent. More preferably, the total combined amounts range from 4.0 to 8.0 weight percent.

"Weak Acid" as used herein is understood herein as an acid that does not dissociate completely in solution, for example, peracetic acid (PAA), acetic acid, boric acid, and phosphoric acid.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

Any compositions or methods provided herein can be combined with one or more of any of the other compositions and methods provided herein.

DETAILED DESCRIPTION AND PREFERRED EMBODIMENTS

The invention provides biocompatible biomaterials, methods for preparation of the biomaterials, and methods for implantation of the biomaterials of the instant invention.

The first class of biocompatible biomaterials provided by the instant invention, cell based biocompatible biomaterials, includes a combination of biomaterial (water, frequently in the form of a hydrogel), and lipid (fat)-soluble molecules in the presence of a surfactant, preferably in conjunction with a scaffold, preferably a biocompatible polymer cross-linkable scaffold. This biomaterial is a fat cell-based biomaterial, and the transplant is preferably from an autologous donor. The extent of mixing can be modified by the surfactant choice and concentration. The fat can be processed as desired and the biomaterial choice can include many of the standard biomaterial components. The importance of combining the water and fat together in the presence of the scaffold is as follows: 1) The scaffold provides a three dimensional framework/scaffold for the cells in the fat to better form tissue (i.e., larger volume). 2) Some biomaterials (i.e., hyaluronic acid) can induce vascularization, which helps fat formation, and provide larger volumes. Since this procedure implantation of the biomaterial of the invention is preferably by injection, multiple injections can be made to build larger tissue structures.

This first class of biocompatible biomaterials allows for the combination of hyaluronic acid, as well as other materials, including hydrogels, with autologous fat through the use of a surfactant system. Such a system allows for the emulsification of hydrophilic biomaterials and lipids into an otherwise immiscible material. The result is an injectable biomaterial with larger volume and enhanced longevity as compared to prior filler materials, thus improving clinical outcome compared to fat or filler transfer alone, while maintaining ease of clinical use and the desired texture.

The invention provides a second class of biocompatible biomaterial which are acellular adipose biocompatible biomaterials also referred to as processed adipose tissue (PAT). The acellular biomaterial is derived from donor adipose tissue, however, as the cellular material is removed from the tissue, it is non-immunogenic and can be used for non-autologous donation. This provides for greater convenience and standardization of biomaterial for use by providing an "off the shelf" biocompatible biomaterial (filler).

The acellular material is produced, for example, by decellularization, preferably chemical decellularization of adipose tissue. Due to the stiffness of the material, mechanical or manual manipulation is performed on the sample at each wash step to insure proper mixing of the processed tissue samples with the wash solutions. Preparation of the acellular adipose biocompatible biomaterial can be accomplished by performance of homogenization and serial washes in sterile saline, preferably followed by serial washes in a solution to further extract the lipid from the cells, for example an organic peroxide such as peracetic acid (about 0.1%-10% v/v, preferably about 0.5% to about 2.5% v/v, preferably about 1% v/v) or a bile acid such as deoxycholic acid (about 0.1%-10% w/v, preferably about 0.5% to about 2.5% w/v, preferably about 1% w/v). The acid wash is optionally followed by serial washes in a non-ionic detergent such as those provided herein including Triton-X 100 or Tween 20 (about 0.1%-10% v/v, preferably about 0.5% to about 2.5% v/v, preferably about 1% v/v) in a buffer such as phosphate buffered saline (PBS) or in water. Optionally, the bile acid, weak acid, and/or non-ionic detergent washes can be followed by washes in an organic solvent such as dichloromethane/methanol (2:1). to remove the remaining lipid in the material and produce a homogeneous white biological scaffold. The material is then sterilized through any appropriate method including, but not limited to, gamma irradiation and/or treatment with ethylene oxide. The processed adipose tissue is the formed into particles of the desired size, preferably to allow for injection, and optionally mixed with the appropriate biomaterials such as polymerizable biopolymer scaffold with or without one or more cross-linking agents prior to injection into the subject. As needed, the injected material is subjected to a cross-linking activator (e.g., an appropriate wavelength of light) after injection. Such considerations are well understood by those of skill in the art.

Previous studies have shown that the extra-cellular-matrix (ECM) components, glycoproteins, and gylcosaminoglycans (GAGs) found in subcutaneous adipose tissue have the potential to induce adipogenesis (Uriel, S., Huang, J., Moya, M. L., et al., The Role of Adipose Derived Protein Hydrogels in Adipogenesis. Biomaterials. Volume 29, 2008, pp 3712-3719, incorporated herein by reference). Taking advantage of the inherent bioactivity of subcutaneous adipose tissue, the invention provides tissue-derived materials by processing adipose tissue to create instructive matrices for adipose tissue reconstruction. The methodologies for the fat tissue treatment depend on removal of cells and lipids that cause inflammatory reactions and local toxic reactions, respectively. The final, processed adipose tissue (PAT) is acellular and contains little to no lipid remnants, yet retains the native architecture and bioactivity of adipose tissue. Similar to the off-the-shelf acellular dermal product, Alloderm™, which is commonly used for skin replacement and hernia repairs, this PAT would provide both volume and a scaffold for in situ tissue formation in soft tissue reconstruction and augmentation.

Figure 1:
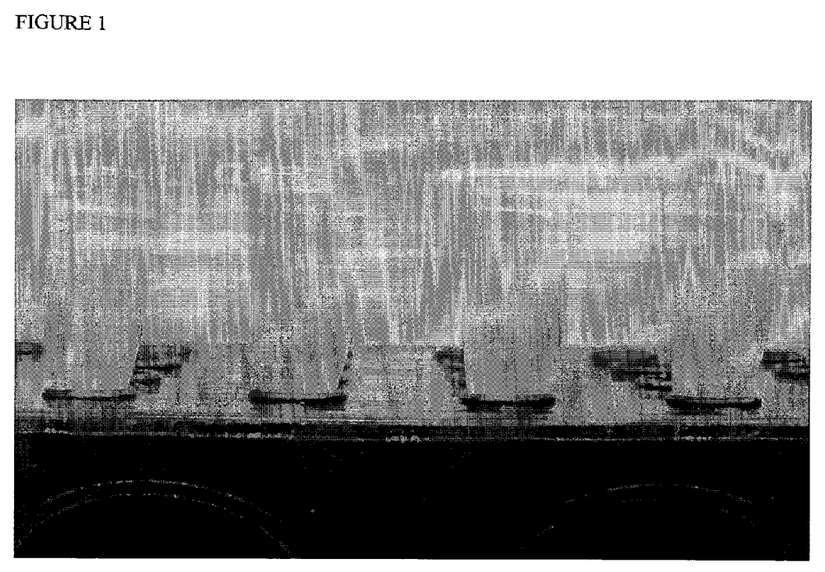
FIG. 1 shows a lipid and aqueous PEG mixture. The far left lane contains no surfactant. Phase separation is evident. Moving to the right, increased concentrations of surfactant have been added demonstrating improved emulsification.
Figure 2:
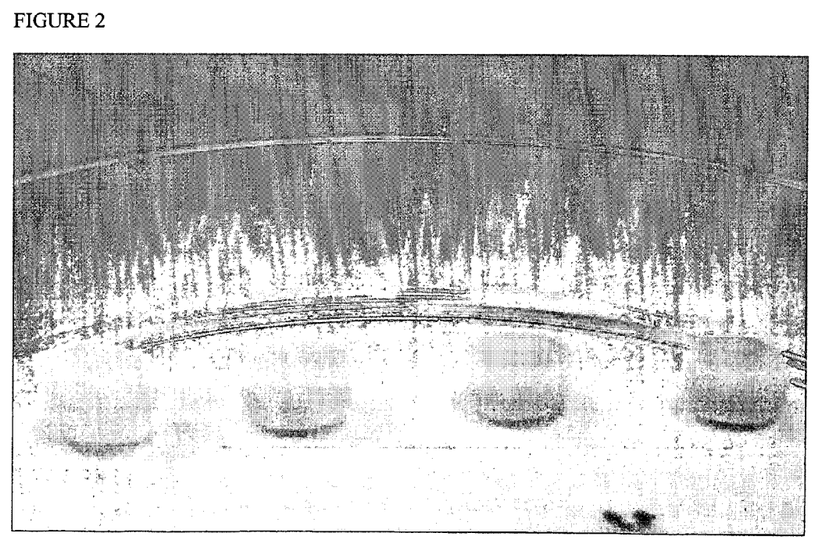
FIG. 2 shows 10% w/v PEG dissolved in varying ratios of lipoaspirate and HA (10%-50%)
Figure 3:
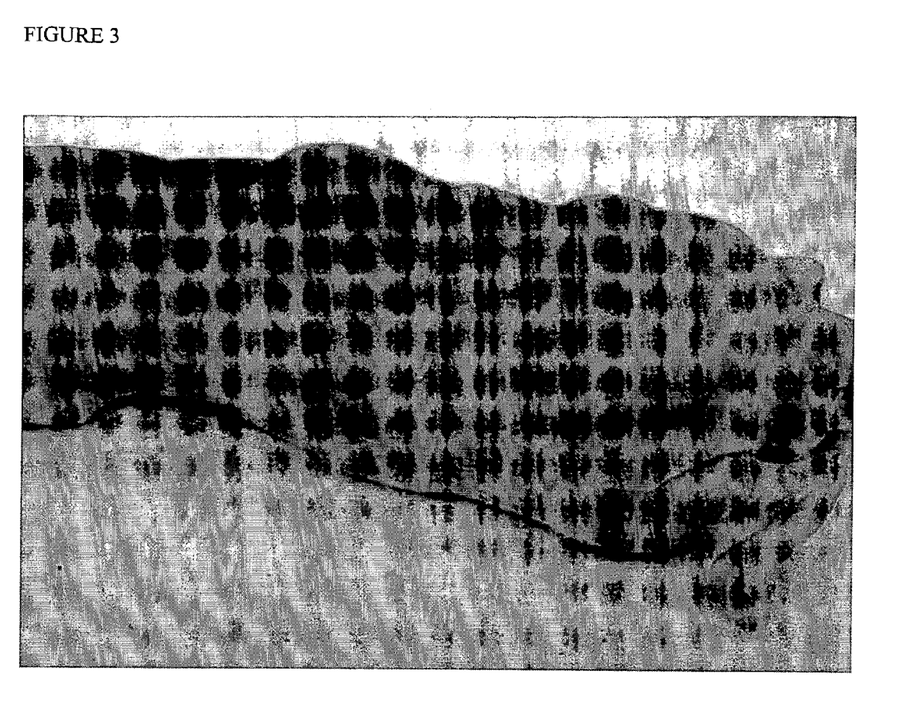
FIG. 3 shows a cross section of tissue after subcutaneous injections of lipoaspirate and PEG and HA in an athymic mouse.
Figure 4:
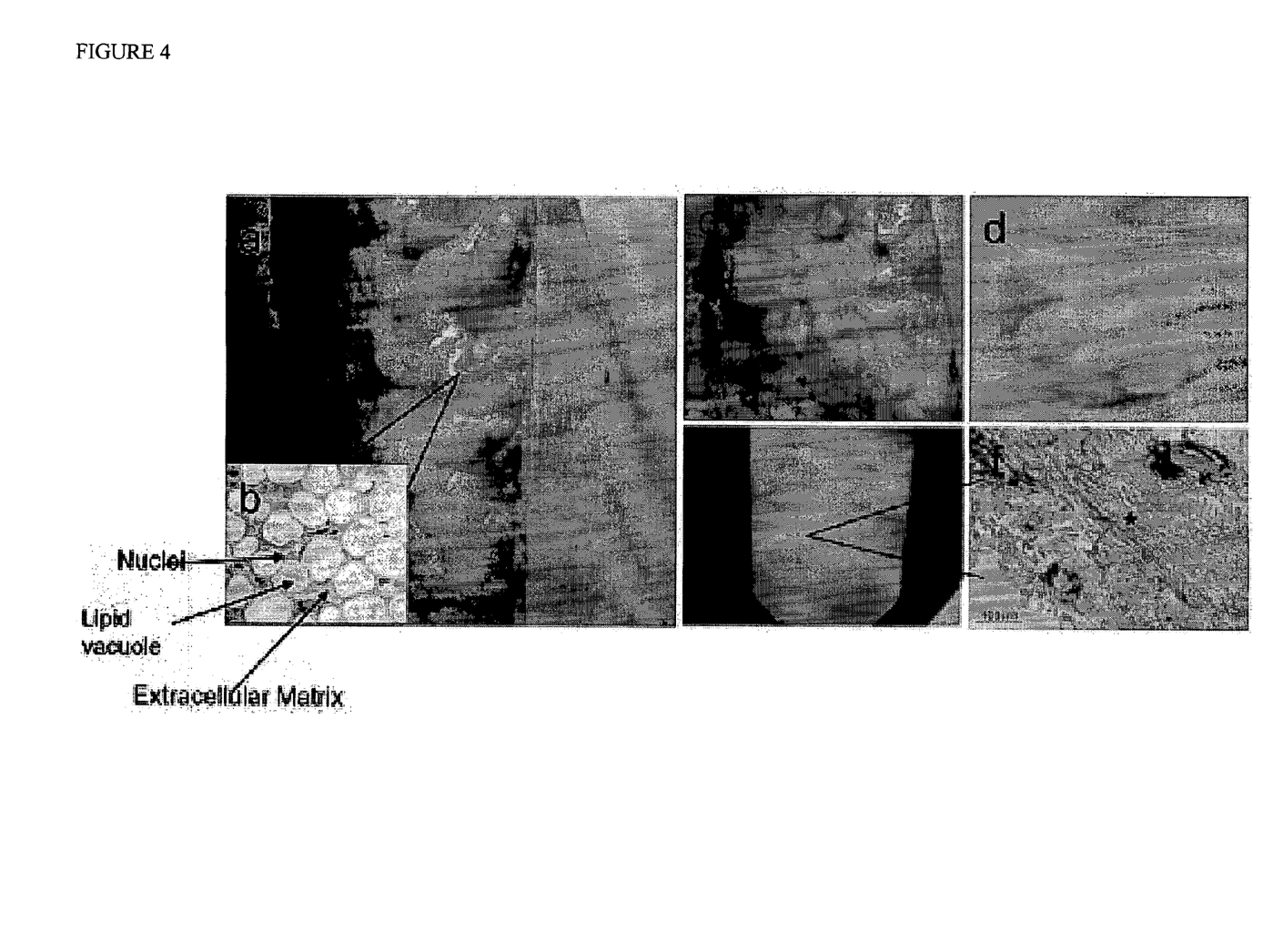
FIGS. 4A-F show an overview of an example of a adipose tissue processing method to generate the acellular adipose biomaterial of the invention. A) Skin from abdominoplasty surgery with underlying subcutaneous adipose tissue; B) Microscopic view of H&E stained histological section of pre-processed adipose tissue, consisting of large, lipid filled, nucleated cells (adipocytes) and surrounding matrix; C-D) Subcutaneous adipose tissue is collected by simple scraping. Various chemical and mechanical processing methods have been employed to obtain a cell and lipid free matrix; E) Gross images of the processed adipose tissue; and F) H&E stained sections of processed adipose tissue. There is no evidence of hematoxylin-staining nuclei, indicating the material is acellular. The large, empty lipid vacuoles seen in pre-processed adipose tissue are absent. The ECM is intact as evidenced by the preserved native fibrillar collagen bundle architecture (*) and vasculature (>)

As demonstrated herein, subcutaneous adipose tissue can be processed to remove cells and lipids, while still preserving the native architecture of the extra-cellular-matrix. Histology of the processed tissue is void of nucleated cells and the lipid vacuoles seen in unprocessed adipose tissue (FIG. 4).

The invention provides for the use of injectable biomaterials, including breast augmentation, to which the biocompatible biomaterials of the invention are uniquely suited. The use of the biomaterials of the invention provide solutions to problems with prior fillers and allow for elimination of scar, reduced surgical and anesthesia time, eliminations of foreign body reaction to a synthetic breast implant, as well as providing a more natural feel, for example in breast reconstruction.

Methods to prolong the persistence of transferred autologous fat have been intensely pursued. Biomaterials have been used for this purpose in numerous tissue types. A major limitation in the application of biomaterials to lipid tissue is the phase separation when mixing hydrophilic biomaterials with lipids. Compositions and methods provided herein overcome these limitations through the use of a surfactant, thus facilitating the application of a variety of biomaterials to lipid tissue. Alternatively, the compositions of the invention provide a scaffold for fat cells without requiring the incorporation of the fat cells into the biomaterial.

The use of currently available commercial fillers is limited by both volume and longevity. Although autologous fat provides greater volume, its use is limited by its low graft survival rate, due in part to cellular necrosis. By developing compositions and methods for combining biomaterial based scaffolds, such as hyaluronic acid or hydrogels to fat, both of these problems are simultaneously addressed. The combination of fat and biomaterials such as biocompatible polymers provides an immediately greater volume of biomaterial. Secondly, the compositions of the invention utilize the dual nature of hyaluronic acid and other biomaterials, behaving as both a scaffold in addition to a biomaterial, therefore providing a network that allows cellular attachment, vascular ingrowth, and interaction with growth factors, which addresses the problem of cellular death believed to be responsible for poor fat graft survival. The PAT of the instant invention can be combined with hyaluronic acid or other biomaterials such as biocompatible polymers and adhesives for use for any of a number of applications.

The invention provides a surfactant system to allow the combination of various hydrophilic scaffolds, including commercially available hyaluronic acid and hydrogels, to hydrophobic adipose tissue to be used in fat transfer. Currently, lipoaspirate is injected in desired locations unprocessed. Through the use of a surfactant system provided herein, it is now possible to appropriately emulsify hydrophilic biomaterials with adipose tissue, prior to re-injection of lipoaspirate. This has the desired effect of enhancing the survival of the autologous fat grafts by providing mature and pre-adipocytes with a scaffold to which to adhere. In addition, the use of a biomaterial scaffold as the delivery agent enables the incorporation of various growth promoting factors to stimulate adipogenesis thereby promoting graft survival, another novelty to current fat transfer techniques Modifications of the invention include the use of various surfactants, provided herein, particularly for use with the cellular biomaterial.

Further modifications include the use of various biomaterials, including Poly(ethylene-glycol) diacrylate (PEG-A), hyaluronic acid (HA) available as commercial fillers including but not limited to Restylane, Juviderm, Captique, Teoxyl.

The invention further provides for the incorporation of Mesenchymal Stem Cells (MSCs), Embryonic Stem Cells (ES), Adipose Tissue Derived Stem Cells (ATDS), fibroblasts as well as other cell types into the biomaterial encapsulated lipoaspirate. Further variations include scaffold modifications to include peptides, hormones, growth factors, vitamins, receptors, drugs, and other regulatory factors. Clinical application includes facial reconstruction, breast reconstruction, injection laryngoplasty, treating HIV protease-induced lipoatrophy, cosmetic surgery including breast, buttock, calf, pectoralis, lip, and cheek augmentation, reversing wrinkles and filling in defects including scars, traumatic injury, congenital defects, surgical scars, burns, and defects from tumor resection.

Crosslinkable Hydrophillic Polymers

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Examples of materials which can be used to form a hydrogel include modified alginates. Alginate is a carbohydrate polymer isolated from seaweed, which can be cross-linked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel, which are derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Charged Crosslinkable Polymer Solutions

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

The preferred anions for cross-linking of the polymers to form a hydrogel are monovalent, divalent or trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically cross-linkable groups. Methods for modifying hydrophilic polymers to include these groups are well known to those of skill in the art.

The polymers may be intrinsically biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 daltons or below. Usable, but less preferable for general use because of intrinsic biodegradability, are water-soluble natural polymers and synthetic equivalents or derivatives, including polypeptides, polynucleotides, and degradable polysaccharides.

The polymers can be a single block with a molecular weight of at least 600, preferably 2000 or more, and more preferably at least 3000. Alternatively, the polymers can include can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Covalently Crosslinkable Polymer Solutions

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., ASAIO Trans., vol. 38, pp. 154-157 (1992).

The term "active species polymerizable group" is defined as a reactive functional group that has the capacity to form additional covalent bonds resulting in polymer interlinking upon exposure to active species. Active species include free radicals, cations, and anions. Suitable free radical polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In one embodiment, the active species polymerizable groups are preferably located at one or more ends of the hydrophilic polymer. In another embodiment, the active species polymerizable groups are located within a block copolymer with one or more hydrophilic polymers forming the individual blocks. The preferred polymerizable groups are acrylates, diacrylates, oligoacrylates, dimethacrylates, oligomethacrylates, and other biologically acceptable photopolymerizable groups. Acrylates are the most preferred active species polymerizable group.

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

Naturally occurring and synthetic polymers may be modified using chemical reactions available in the art and described, for example, in March, "Advanced Organic Chemistry," 4th Edition, 1992, Wiley-Interscience Publication, New York. Such methods may be used to, for example, introduce acrylate groups as described herein.

Preferably, the hydrophilic polymers that include active species or crosslinkable groups include at least 1.02 polymerizable or crosslinkable groups on average, and, more preferably, each includes two or more polymerizable or crosslinkable groups on average. Because each polymerizable group will polymerize into a chain, crosslinked hydrogels can be produced using only slightly more than one reactive group per polymer (i.e., about 1.02 polymerizable groups on average). However, higher percentages are preferable, and excellent gels can be obtained in polymer mixtures in which most or all of the molecules have two or more reactive double bonds. Poloxamines, an example of a hydrophilic polymer, have four arms and thus may readily be modified to include four polymerizable groups.

Methods of Implantation

In a preferred embodiment, the compositions of the invention are prepared and injected directly into a site where it is desired to implant the material. If a cross-linking agent is to be used, the material is preferably injected prior to cross-linking of the polymer to form the hydrogel. In a preferred method, the crosslinking occurs sufficiently rapidly such that there is no substantial migration of the biomaterial away from the site of injection. In particular embodiments, it may be advantageous to deliver the biomaterial by multiple injections, either at multiple sites or at periodic time intervals, intervals of minutes, hours, days, weeks, or longer. Periodic implantation may be required to allow the skin to stretch to accommodate the biomaterial (e.g., during breast reconstruction after mastectomy).

The site, or sites, where the biomaterials of the invention are to be injected is determined based on individual need, as is the requisite number of cells when the biomaterial contains cells. One can apply an external mold to shape the injected solution. Additionally, by controlling the rate of polymerization, it is possible to mold the biomaterial injected implant like one would mold clay. Alternatively, the mixture can be injected into a mold, the biomaterial allowed to harden, then the material implanted.

The composition can be injected via a syringe and needle directly into a specific area wherever a bulking agent is desired, i.e., a soft tissue deformity such as that seen post-operatively or with areas of muscle atrophy due to congenital or acquired diseases or secondary to trauma, burns, and the like. An example of this would be the injection of the composition in the breast area after mastectomy or in the upper torso of a patient with muscular atrophy secondary to nerve damage.

The suspension can also be injected percutaneously by direct palpation, such as by placing a needle inside the vas deferens and occluding the same with the injected bulking substance, thus rendering the patient infertile. The suspension can also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required. Further, this substance could be injected through a laparoscope or thoracoscope to any intraperitoneal or extraperitoneal or thoracic organ.

Optionally, various additives can be included in the hydrogel solution such as 100 U/ml of penicillin and 100 µg/ml streptomycin to inhibit microbacterial contamination. However, these are not the only bioactive additives that can be included in the hydrogel solution. For example, the bioactive additives could include, singly or in combination, growth factors, cell differentiation factors, other cellular mediators, nutrients, antibiotics, antiinflammatories, and other pharmaceuticals. Although not limiting, some suitable cellular growth factors, depending upon the cell type to be encapsulated in either the hydrogel of the same or adjacent hydrogel layer, include heparin binding growth factor (HBGF), transforming growth factor (TGFα or TGFβ), alpha fibroblastic growth factor (FGF), epidermal growth factor (EGF), vascular endothelium growth factor (VEGF), various angiogenic factors, growth factors, nerve growth factor (NGF), and muscle morphologic growth factor.

In addition, the hydrogel solution optionally includes a suitable non-toxic polymerization initiator, mixed thoroughly to make a final concentration of 0.05% w/v. When PEGDA or PEODA are selected as the polymers, the polymerization initiator is preferably added and selected to be the photoinitiator Igracure™ 2959 (commercially available from Ciba Specialty Chemicals Corp., Tarrytown, N.Y.), although other suitable photoinitiators can be used.

While photopolymerizable PEGDA and PEODA are among the preferred polymers for making hydrogels in accordance with the present invention, other suitable hydrophilic polymers can be used. Suitable hydrophilic polymers include synthetic polymers such as partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof. This list of photopolymerizable mixtures is meant to be illustrative and not exhaustive. For example, other photopolymerizable mixtures suitable for application in the present invention are described in U.S. Pat. No. 6,224,893 B1, which is incorporated herein by reference.

While a preferred photoinitiator is Igracure™ 2959, various other photoinitiators can be used instead. For example, HPK, which is commercially available from Polysciences, is another suitable photoinitiator. In addition, various dyes and an amine catalyst are known to form an active species when exposed to external radiation. Specifically, light absorption by the dye causes the dye to assume a triplet state, which subsequently reacts with the amine to form the active species that initiates polymerization. Typically, polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used for photopolymerization, and these include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst with one of these dyes. Photopolymerization of these polymer solutions is based on the knowledge that combinations of polymers and photoinitiators (in a concentration not toxic to the cells, less than 0.1% by weight, more preferably between 0.05 and 0.01% by weight percent initiator) will crosslink upon exposure to light equivalent to between one and 3 mWatts/cm$^2$.

While photopolymers are preferred for making the hydrogels, because it is convenient to control polymerization using external radiation supplied through a surgical scope, the present invention can be practiced using other polymer materials and polymerization initiators. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thiotropic and form a gel over time by the slow evolution of structure, and (d) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention, and this patent is incorporated herein by reference in its entirety.

Polymerizable agents for use in the instant invention may comprise monomers, macromers, oligomers, polymers, or a mixture thereof. The polymer compositions can consist solely of covalently crosslinkable polymers, or blends of covalently and ionically crosslinkable or hydrophilic polymers.

EXAMPLE 1

Preparation of a Cellular Biocompatible Biomaterial

A lipoaspirate was obtained using standard minimally invasive surgical techniques. Tumescent fluid was removed and the lipoaspirate was placed on ice until next step. The lipoaspirate was combined with various surfactants and scaffolds for the preparation of the biocompatible biomaterial.

1. Hyaluronic acid was emulsified with lipoaspirate in a 1:1 ratio with the addition of 5% Pluronic surfactant.

2. A 10% weight per volume PEG-DA was dissolved in a 50:50 ratio of PBS:Lipoaspirate.

The HA used was a commercially available crosslinked HA which requires no cross-linker and can be molded by hand.

A photoinitiator was prepared and added for the polymerization of the PEG-DA mixture. Initiator solution was prepared by dissolving eosin Y disodium salt (Sigma-Aldrich CAT# 45235, which absorbs most strongly in the 450-550 nm wavelength range) in PBS (GIBCO CAT# 14190342) (1.375 mg/ml Eosin Y). 100 mg (10% w/v) PEODA (3.4 KD MW SunBio CAT# P2AC-3) was dissolved in 50 µl of initiator solution, 30 µl of PBS, and 20 µL of N-vinyl pyrrolidone (Sigma-Aldrich CAT# 95060). Final solutions were prepared by mixing this PEODA solution with 30 µl of triethanolamine (Sigma-Aldrich #90278) and 1 ml of lipoaspirate The mixtures were vortexed until mixture appeared to have a homogeneous distribution of fat.

The HA mixture was injected subcutaneously.

The PEG-DA/liopaspirate mixture was injected subcutaneoulsy and a light source (e.g., light emitting diode) was applied to provide Intense Pulsed Light (IPL) in the case of hydrogel. Methods for transdermal photopolymerization are well known in the art (see, e.g., Elisseeff et al, Transdermal photopolymerization for minimally invasive implantation, *Proc. Natl. Acad. Sci, USA*. 96:3104-3107, incorporated herein by reference).

EXAMPLE 2

Preparation of Acellular Biomaterial/Processed Adipose Tissue (PAT)

Tissue acquisition and processing. Tissue was acquired from fresh surgical and cadaveric sources with appropriate consent of the donors. A representative sample of subcutaneous fat is shown in FIG. 4A. A representative histological section showing nuclei, lipid vacuoles, and extracellular matrix is provided in FIG. 4B. Subcutaneous fat was isolated from the sample by scraping and transferred to a tube for solubilization using peracetic acid (PAA) or deoxycholic acid to promote chemical decellularization. As adipocytes die, oil is released from the cells, and the material is washed with phosphate buffered saline (PBS) to remove debris and bring the pH back to physiological pH. To fully infiltrate the adipose tissue and remove the oil, the material is manually manipulated with a mortar and pestle, or homogenized in a blender or with a press between washes with PBS. As the lipid is removed, the processed adipose material changes from yellow to white. The processed adipose material can be monitored for removal of cell and lipid material using the methods provided herein. The processed adipose material is then sterilized, for example using irradiation, and made into particles for injection with or without a biopolymer scaffold and cross-linking agents.

EXAMPLE 3

Analysis of Acellular Biocompatible Biomaterial

The acellular biocompatible biomaterial has been tested using a number of assays to demonstrate that the material is acellular, lipid-free, includes intact extracellular matrix (ECM), and the appropriate dynamic stiffness. Exemplary assays used are provided. Other methods to determine if the material has the desired characteristics are known in the art.

Cell Free. Hematoxylin and eosin (H&E) staining was performed on paraffin-embedded sections of PAT prepared by at least one of the methods of the previous example to determine the presence of nuclei (cells) (FIG. 4F). No cellular material or nuclei were observed.

In addition, MHC class I immunostaining is performed to evaluate the presence of antigens. DNA assay has been used to quantify nuclear contents in the tissue. Briefly, for fluorometric DNA assays, calf thymus DNA standards were prepared 0-100 µg/ml DNA. Samples (30 µl of digested tissue) or standards were mixed with 33258 Hoechst solution (0.1 µg/ml, Molecular probes, Eugene, Oreg.) dissolved in 1XTNE buffer (10 mM Tris, 1 mM EDTA, 0.2 M NaCl, pH. 7.4). DNA content is determined with a fluorometer using A365 nm excitation and A458 nm emission, and calculated from the calf thymus DNA standard curve.

Lipid Free. A rapid emulsion assay has been conducted to rule out the presence of residual lipids in the processed tissue, followed by a more quantitative triglyceride ELISA (Wako Chemical, Japan). The presence of lipids can also be observed histologically (see FIG. 4F). No lipid was observed.

ECM Preservation. Extracellular matrix preservation has been evaluated histologically to assess architecture (H&E and Trichome stain) (FIG. 4F), quantitatively, using a collagen and proteoglycan biochemical assay, and mechanically. Intact ECM was observed.

Briefly, total collagen content is determined by measuring the hydroxyproline concentration of the papain-digests (100 µl) after hydrolysis with 6 N hydrochloric acid at 110° C. overnight and reaction with p-dimethylaminobenzaldehyde and chloramine-T using 0.1 as the ratio of hydroxyproline to total collagen as described previously (Creemers, L. B., et al., Microassay for the assessment of low levels of hydroxyproline. *Biotechniques*. 22:656-658, 1997; Woessner, J. F., Jr., The determination of hydroxyproline in tissue and protein samples containing small proportions of this imino acid. *Arch Biochem Biophys*. 93: 440-4477, 1961, both incorporated herein by reference).

Determination of proteoglycan concentration is performed on papain digests by the dimethylmethylene blue (DMMB) spectrophotometric assay as previously described. Chondroitin sulfate C (shark cartilage extract, Sigma) is used as the standard.

Dynamic stiffness and compressive moduli of samples are measured using the ELF™ 3200 test instrument. Statistical analysis is performed with the SPSS (version 10.0; SPSS, Chicago, Ill.) software package.

EXAMPLE 4

Assessment of Adipogenicity In Vitro

The processed adipose tissue is assessed for the ability to support cell growth and adipogenesis in vitro. Materials that have achieved the above conditions will then be tested for their ability to support adipogenesis in vitro. Briefly, samples of the processed materials are seeded with human subcutaneous pre-adipocytes and cultured in adipogenic media. Live/Dead assay (Molecular Probes) are performed to demonstrate that the PAT supports cell viability. Oil red O lipid staining of cryosections is performed to confirm adipocyte differentiation and tissue formation. RNA is extracted from cells seeded on the PAT and RT-PCR for adipose markers including PPAR-γ and Lipo-Protein-Lipase (LPL) is performed and compared to cells expanded in monolayer and those in native adipose tissue as described (Hillel, A., et. al. Embryonic Germ Cells are capable of Adipogenic Differentiation in Vitro and in Vivo. *Tissue Engineering* Part A.14:1-8, 2008).

EXAMPLE 5

Assessment of In Vivo Persistence and Tolerability of Cellular Biomaterial

To enable and predict clinical efficacy of the biocompatible biomaterials of the instant invention, a preclinical animal model has been developed and validated to predict the lifetime or persistence and tolerability of soft tissue substitutes. The persistence of subcutaneous injections of various soft tissue materials, including human adipose tissue and commercially available hyaluronic acid dermal fillers, in both athymic mice and Sprague-Dawley rats, correlates with the known clinical persistence of these materials. Persistence of the cell based biomaterials of the invention have been confirmed using MRI volumetric measurements. However, assessment can also be performed using calipers to determine height and width of the injected material.

Figure 5:
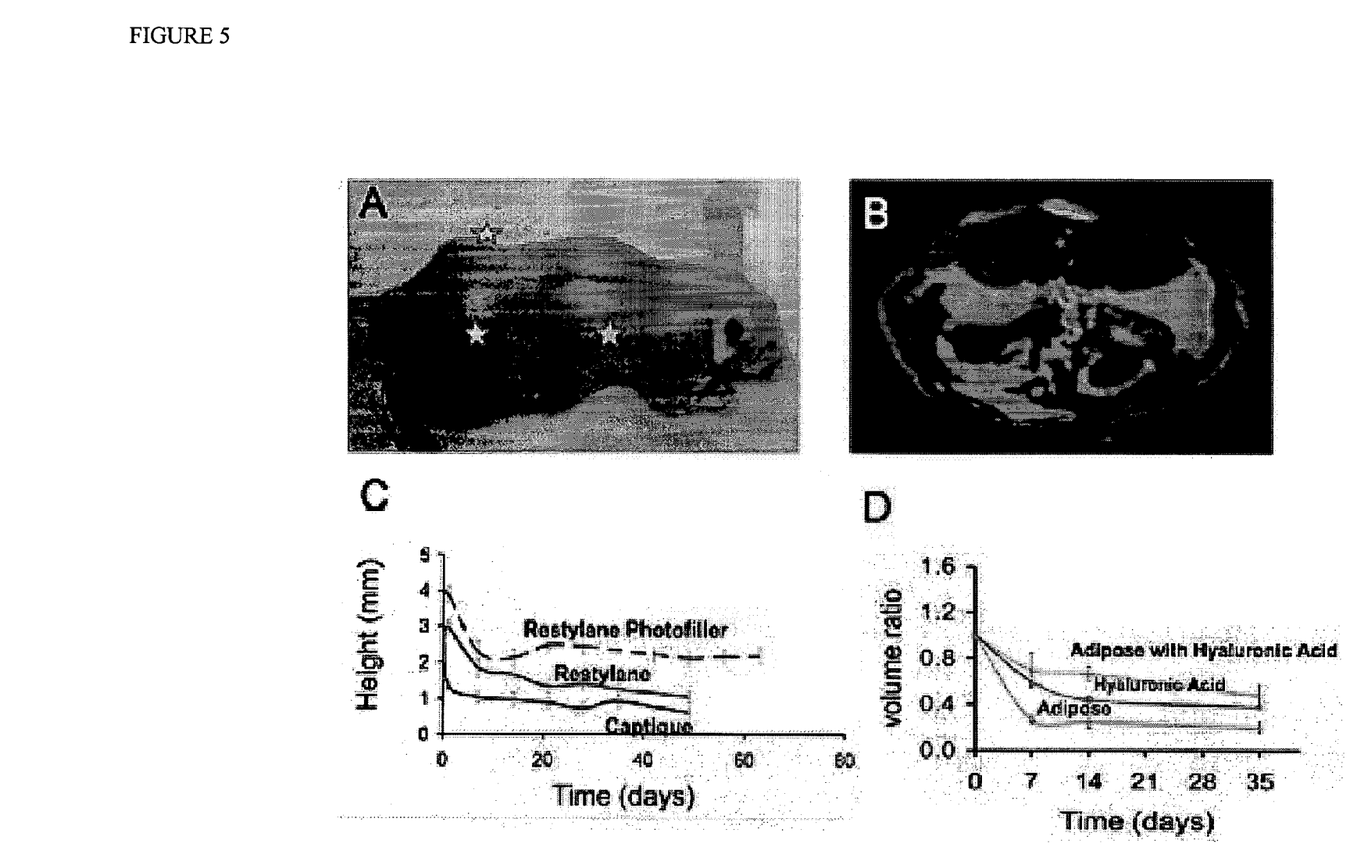
FIGS. 5A-D show A) a gross image of soft tissue implants on the dorsum of an athymic nude mouse; B) T2 MRI of a Sprague-Dawley rat with soft tissue implants, allowing for volumetric measurements; and C-D) Height and volume of implants are plotted over time and have been found to correlate with known clinical persistence of implanted adipose tissue and commercially available injected dermal fillers.
Figure 6A:
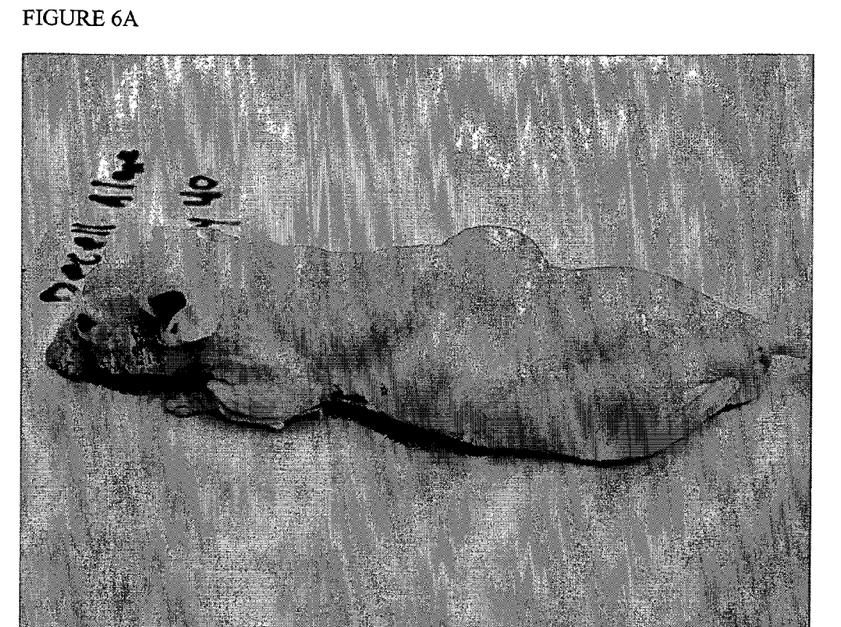
FIGS. 6A-D show A-B) gross images of implanted processed adipose tissue in an athymic mouse 40 days after implantation; C) Implanted processed adipose tissue in a rat at day 45; and D) 4×H&E stain of processed adipose tissue following implantation in a rat at day 45.
Figure 6B:
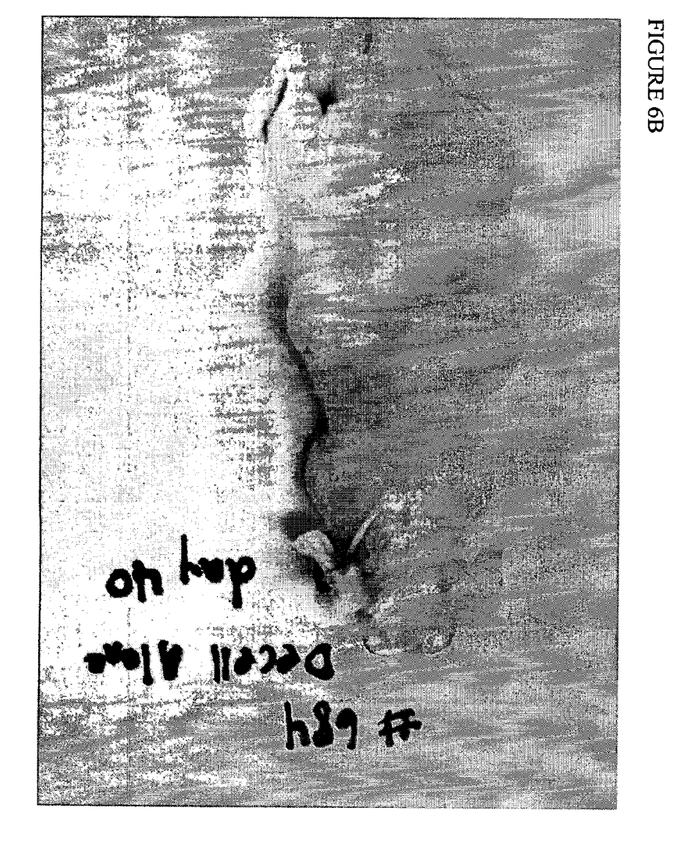
Figure 6C:
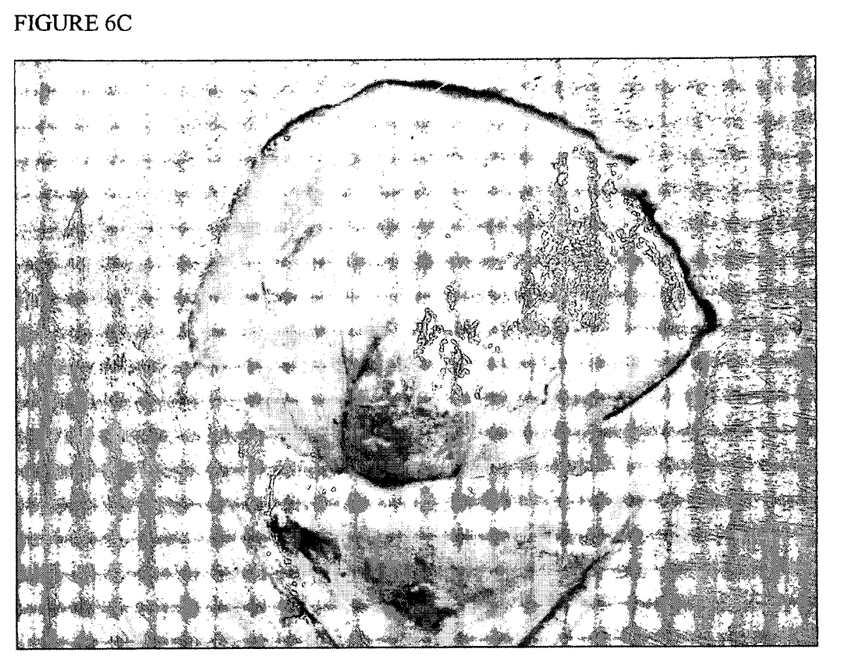
Figure 6D:
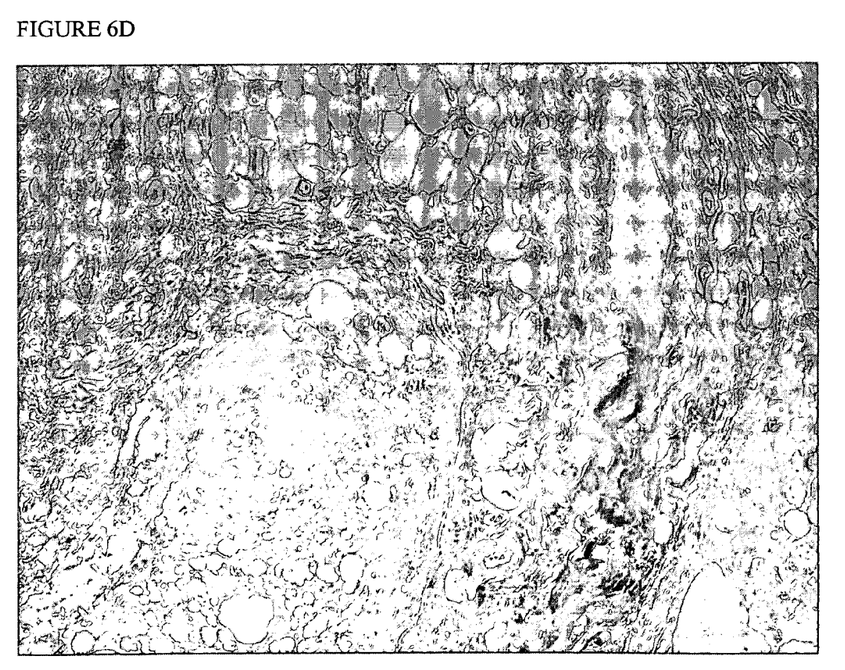

Equal volumes of material for assessment was injected into the back of an athymic nude mouse (see FIG. 5). The persistence of commercially available fillers was tested over a several weeks. Height of implants in mm was measured at regular intervals and plotted over time (see FIG. 5C). Captique®, a non-animal stabilized hyaluronic acid (Inamed Corporation and Genzyme Corporation) a facial wrinkle correction filler, was found to lose height most rapidly in the assay. Restylane®, a stabilized hyaluronic acid gel was found maintain height for longer than Captique®, and its ability to maintain height was improved by the addition of PEG-DA.

A similar assay was performed using the cellular adipose biomaterial of the instant invention as compared to injection of lipoaspirate alone and HA alone (commercially available, Hylaform) were compared to HA (Hylaform) after being mixed with Lipoaspirate. Volume was assessed using MRI. Adipose tissue with hyaluronic acid was found to maintain significant volume over the course of the study. Hyaluronic acid alone, or adipose alone were found to dissipate more rapidly (see FIG. 5C-D).

EXAMPLE 6

Assessment In Vivo of Processed Adipose Tissue

One milliliter of processed adipose tissue was implanted subcutaneously on the dorsum of a Sprague-Dawley rat and 500 ul on an athymic nude mouse. The implants were monitored over time via palpation and measurements were taken using a caliper and found to persist at 45 days from the time of implantation. At day 45, the animals were sacrificed and the material was harvested for histology. Histology demonstrated evidence of integration with surrounding tissue, angiogenesis, and minimal inflammation (see FIGS. 6A-D).

Those skilled in the art will recognize, or be able to ascertain using no more than routine experimentation, many equivalents to the specific embodiments of the invention described herein. Such equivalents are intended to be encompassed by the following claims.

All references, patents, and patent publications cited herein are incorporated herein by reference as if they were each incorporated individually.

We claim:
1. A method for preparation of an acellular adipose biocompatible biomaterial or processed adipose tissue (PAT) consisting of sequentially:
   a) providing mammalian tissue comprising solid adipose tissue;
   b) isolating the adipose tissue from the non-adipose tissue;
   c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
   d) washing the adipose tissue of c) by contacting the adipose tissue with a buffer and manipulating the adipose tissue in the presence of the buffer to remove the decellularization agent of c) and promote lipid and cell removal;
   e) optionally repeating steps c) and d) one or more times; and
   f) obtaining an acellular adipose biocompatible biomaterial which is acellular, lipid-free and retains the existing native structure and bioactivity of the extracellular matrix.

2. A method for preparation of an acellular adipose biocompatible biomaterial or processed adipose tissue (PAT) consisting of sequentially:
   a) providing mammalian tissue comprising solid adipose tissue;
   b) isolating the adipose tissue from the non-adipose tissue;
   c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
   d) washing the adipose tissue of c) by contacting the adipose tissue with a buffer and manipulating the adipose tissue in the presence of the buffer to remove the decellularization agent of c) and promote lipid and cell removal;
   e) optionally repeating steps c) and d) one or more times;
   f) contacting the adipose tissue of d) with a solution comprising a non-ionic detergent and manipulating the adipose tissue in the presence of the solution, followed by washing the adipose tissue by contacting the adipose tissue with a buffer and manipulating the adipose tissue in the presence of the buffer to remove the non-ionic detergent and promote lipid and cell removal; and
   g) obtaining an acellular adipose biocompatible biomaterial which is acellular, lipid-free and retains the existing native structure and bioactivity of the extracellular matrix.

3. A method for preparation of an acellular adipose biocompatible biomaterial or processed adipose tissue (PAT) consisting of sequentially:
   a) providing mammalian tissue comprising solid adipose tissue;
   b) isolating the adipose tissue from the non-adipose tissue;
   c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
   d) washing the adipose tissue of c) by contacting the adipose tissue with a buffer and manipulating the adipose tissue in the presence of the buffer to remove the decellularization agent of c) and promote lipid and cell removal;
   e) optionally repeating steps c) and d) one or more times;
   f) obtaining an acellular adipose biocompatible biomaterial which is acellular, lipid-free and retains the existing native structure and bioactivity of the extracellular matrix; and g) combining the processed adipose tissue with a biopolymer scaffold.

4. A method for preparation of an acellular adipose biocompatible biomaterial or processed adipose tissue (PAT) consisting of sequentially:
- a) providing mammalian tissue comprising solid adipose tissue;
- b) isolating the adipose tissue from the non-adipose tissue;
- c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
- d) washing the adipose tissue of c) by contacting the adipose tissue with a buffer and manipulating the adipose tissue in the presence of the buffer to remove the decellularization agent of c) and promote lipid and cell removal;
- e) optionally repeating steps c) and d) one or more times;
- f) obtaining an acellular adipose biocompatible biomaterial which is acellular, lipid-free and retains the existing native structure and bioactivity of the extracellular matrix;
- g) combining the processed adipose tissue with a biopolymer scaffold; and
- h) combining the processed adipose tissue with a cross-linking agent.

5. A method for preparation of an acellular adipose biocompatible biomaterial or processed adipose tissue (PAT) consisting of sequentially:
- a) providing mammalian tissue comprising solid adipose tissue;
- b) isolating the adipose tissue from the non-adipose tissue;
- c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
- d) washing the adipose tissue of c) by contacting the adipose tissue with a buffer and manipulating the adipose tissue in the presence of the buffer to remove the decellularization agent of c) and promote lipid and cell removal;
- e) optionally repeating steps c) and d) one or more times;
- f) obtaining an acellular adipose biocompatible biomaterial which is acellular, lipid-free and retains the existing native structure and bioactivity of the extracellular matrix; and
- g) sterilizing the acellular adipose biocompatible biomaterial of e) by gamma irradiation or exposure to ethylene oxide gas.

6. A method for preparation of an acellular adipose biocompatible biomaterial or processed adipose tissue (PAT) consisting of sequentially:
- a) providing mammalian tissue comprising solid adipose tissue;
- b) isolating the adipose tissue from the non-adipose tissue;
- c) decellularizing the adipose tissue and extracting lipid from the adipose tissue by contacting the adipose tissue with a decellularization agent selected from the group consisting of a weak acid, a weak organic acid, and a bile acid and manipulating the adipose tissue in the presence of the decellularization agent;
- d) washing the adipose tissue of c) by contacting the adipose tissue with a buffer and manipulating the adipose tissue in the presence of the buffer to remove the decellularization agent of c) and promote lipid and cell removal;
- e) optionally repeating steps c) and d) one or more times;
- f) contacting the adipose tissue of d) with a solution comprising a non-ionic detergent and manipulating the adipose tissue in the presence of the solution, followed by washing the adipose tissue by contacting the adipose tissue with a buffer and manipulating the adipose tissue in the presence of the buffer to remove the non-ionic detergent and promote lipid and cell removal;
- g) contacting the washed adipose tissue with a solution comprising an organic solvent and manipulating the adipose tissue in the presence of the solvent, followed by washing the adipose tissue by contacting the adipose tissue with a buffer and manipulating the adipose tissue in the presence of the buffer to remove the solvent; and
- h) obtaining an acellular adipose biocompatible biomaterial which is acellular, lipid-free and retains the existing native structure and bioactivity of the extracellular matrix.

\* \* \* \* \*